US011432797B2

(12) United States Patent
Taniguchi (10) Patent No.: US 11,432,797 B2
(45) Date of Patent: Sep. 6, 2022

(54) ULTRASOUND ENDOSCOPE AND ULTRASOUND ENDOSCOPE SYSTEM

(71) Applicant: OLYMPUS CORPORATION, Tokyo (JP)

(72) Inventor: Yuko Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 778 days.

(21) Appl. No.: 16/353,008

(22) Filed: Mar. 14, 2019

(65) Prior Publication Data

US 2019/0209124 A1    Jul. 11, 2019

Related U.S. Application Data

(63) Continuation of application No. PCT/JP2017/014967, filed on Apr. 12, 2017.

(30) Foreign Application Priority Data

Sep. 15, 2016 (JP) .............................. JP2016-180740

(51) Int. Cl.
| | |
|---|---|
| *A61B 8/12* | (2006.01) |
| *A61B 1/05* | (2006.01) |
| *A61B 1/00* | (2006.01) |
| *A61B 8/00* | (2006.01) |
| *A61B 1/018* | (2006.01) |
| *A61B 8/08* | (2006.01) |
| *A61B 1/005* | (2006.01) |

(52) U.S. Cl.
CPC ............ *A61B 8/12* (2013.01); *A61B 1/00177* (2013.01); *A61B 1/05* (2013.01); *A61B 1/051* (2013.01);
(Continued)

(58) Field of Classification Search
None
See application file for complete search history.

(56) References Cited

U.S. PATENT DOCUMENTS

| | | |
|---|---|---|
| 2006/0009681 A1 | 1/2006 | Tanaka et al. |
| 2008/0271189 A1* | 10/2008 | Hellewell ................ A01H 5/10 800/263 |

(Continued)

FOREIGN PATENT DOCUMENTS

| | | |
|---|---|---|
| CN | 1718165 A | 1/2006 |
| CN | 103841879 A | 6/2014 |

(Continued)

OTHER PUBLICATIONS

International Search Report dated Jun. 27, 2017 issued in PCT/JP2017/014967.

(Continued)

*Primary Examiner* — Shahdeep Mohammed
(74) *Attorney, Agent, or Firm* — Scully, Scott, Murphy & Presser, P.C.

(57) ABSTRACT

An ultrasound endoscope, includes: an insertion portion configured to be inserted into a subject, acquire an optical subject image, and transmit and receive ultrasound; an ultrasound transducer configured to emit the ultrasound in a direction perpendicular to a longitudinal direction of the insertion portion, and perform scanning in a circumferential direction of an axis parallel to the longitudinal direction; a forward field optical portion that is provided at a distal end of the insertion portion in the longitudinal direction, the distal end being where observation light coming from a forward field enters; and a side field optical portion that is provided at a distal end side of the insertion portion in the longitudinal direction and is where observation light from a side field including a part of a scan plane of the ultrasound transducer enters, the side field being a field in a direction perpendicular to the longitudinal direction.

16 Claims, 10 Drawing Sheets

(52) U.S. Cl.
CPC ............ *A61B 8/085* (2013.01); *A61B 8/4461* (2013.01); *A61B 1/00009* (2013.01); *A61B 1/0051* (2013.01); *A61B 1/00082* (2013.01); *A61B 1/018* (2013.01)

(56) References Cited

U.S. PATENT DOCUMENTS

| | | |
|---|---|---|
| 2014/0204187 A1 | 7/2014 | Sasaki et al. |
| 2014/0347878 A1 | 11/2014 | Honda et al. |
| 2016/0361044 A1* | 12/2016 | Hibi ...................... A61B 8/467 |

FOREIGN PATENT DOCUMENTS

| | | | |
|---|---|---|---|
| CN | 104203070 | A | 12/2014 |
| JP | S63264048 | A | 10/1988 |
| JP | H01204654 | A | 8/1989 |
| JP | H02265533 | A | 10/1990 |
| JP | H03057441 | A | 3/1991 |
| JP | 2798710 | B2 | 9/1998 |
| JP | 2001314404 | A | 11/2001 |
| JP | 2006271493 | A | 10/2006 |

OTHER PUBLICATIONS

Chinese Office Action dated Apr. 2, 2021 received in 201780056656.7.

\* cited by examiner

ULTRASOUND ENDOSCOPE AND ULTRASOUND ENDOSCOPE SYSTEM

CROSS-REFERENCE TO RELATED APPLICATION

This application is a continuation of PCT International Application No. PCT/JP2017/014967 filed on Apr. 12, 2017 which claims the benefit of priority from Japanese Patent Application No. 2016-180740, filed on Sep. 15, 2016, the entire contents of which are incorporated herein by reference.

BACKGROUND

1. Technical Field

The present disclosure relates to an ultrasound endoscope and an ultrasound endoscope system, each including: a radial ultrasound transducer that emits ultrasound to a target to be observed, receives ultrasound echoes reflected by the target to be observed, converts the ultrasound echoes into an echo signal, and outputs the echo signal; and an optical system for in-vivo observation of a subject.

2. Related Art

Ultrasound may be applied to observation of characteristics of a body tissue or a material, which is a target to be observed. Specifically, by performing predetermined signal processing on ultrasound echoes received from an ultrasound transducer that transmits and receives ultrasound, an ultrasound observation device is able to acquire information related to characteristics of a target to be observed.

An ultrasound transducer includes plural piezoelectric elements, each of which converts an electric pulse signal into ultrasound pulses (acoustic pulses), emits the ultrasonic pulses to a target to be observed, converts ultrasonic echoes reflected by the target to be observed into an electric echo signal, and outputs the electric signal. For example, by arranging plural piezoelectric elements along a predetermined direction, and electronically changing the piezoelectric elements involved in transmission and reception or delaying transmission and reception by the piezoelectric elements, ultrasound echoes are acquired from a target to be observed.

Different types of ultrasound transducers having different ultrasound beam transmission and reception directions, such as the convex type, the linear type, and the radial type, have been known. Among these, a radial ultrasound transducer has plural piezoelectric elements that are arranged around a predetermined axis and emit ultrasound beams in radial directions orthogonal to the predetermined axis. For example, disclosed in Japanese Patent Application Laid-open No. 2001-314404 and Japanese Patent Application Laid-open No. 2006-271493 are ultrasound endoscopes each including an insertion portion having a radial ultrasound transducer and a forward viewing optical system for in-vivo observation of a subject. In each of the ultrasound endoscopes disclosed in Japanese Patent Application Laid-open No. 2001-314404 and Japanese Patent Application Laid-open No. 2006-271493, a scan plane of the radial ultrasound transducer is orthogonal to a longitudinal direction of the insertion portion, and an optical axis of the forward viewing optical system is parallel to the longitudinal direction of the insertion portion.

SUMMARY

In some embodiments, an ultrasound endoscope, includes: an insertion portion configured to be inserted into a subject, acquire an optical subject image, and transmit and receive ultrasound; an ultrasound transducer configured to emit the ultrasound in a direction perpendicular to a longitudinal direction of the insertion portion, and perform scanning in a circumferential direction of an axis parallel to the longitudinal direction; a forward field optical portion that is provided at a distal end of the insertion portion in the longitudinal direction, the distal end being where observation light coming from a forward field enters; and a side field optical portion that is provided at a distal end side of the insertion portion in the longitudinal direction and is where observation light from a side field including a part of a scan plane of the ultrasound transducer enters, the side field being a field in a direction perpendicular to the longitudinal direction.

The above and other features, advantages and technical and industrial significance of this disclosure will be better understood by reading the following detailed description of presently preferred embodiments of the disclosure, when considered in connection with the accompanying drawings.

DETAILED DESCRIPTION

Described hereinafter by reference to the drawings are modes for carrying out the disclosure (hereinafter, embodiments). The disclosure is not limited by the embodiments described below. Furthermore, throughout the drawings, any identical parts will be assigned with the same reference sign.

First Embodiment

Figure 1:
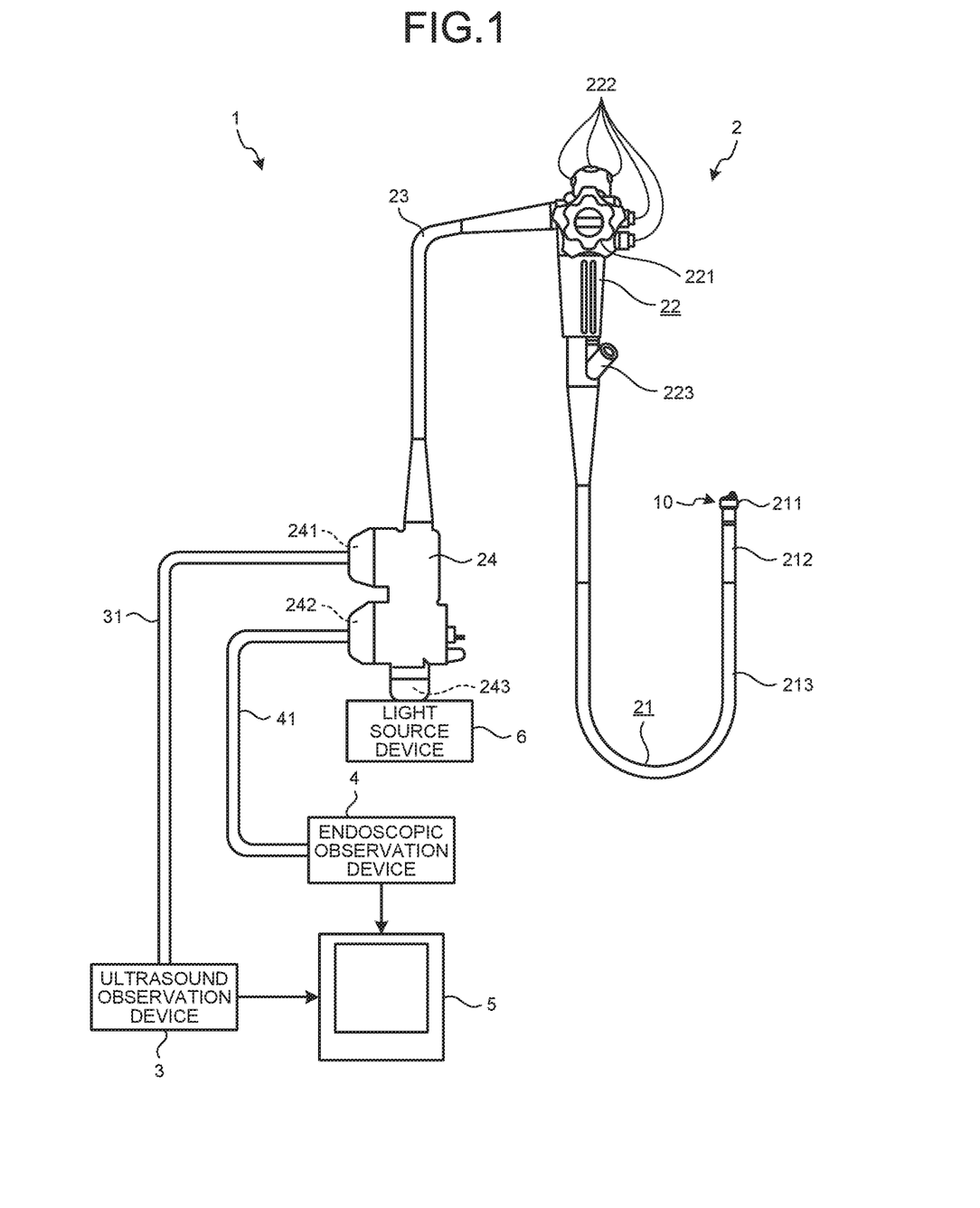
FIG. 1 is a diagram schematically illustrating an endoscope system according to a first embodiment of the disclosure.

FIG. 1 is a diagram schematically illustrating an endoscope system according to a first embodiment of the disclosure. An endoscope system 1 is a system where in-vivo ultrasound diagnosis of a subject, such as a human, is performed by using an ultrasound endoscope. This endoscope system 1 includes, as illustrated in FIG. 1, an ultrasound endoscope 2, an ultrasound observation device 3, an endoscopic observation device 4, a display device 5, and a light source device 6.

The ultrasound endoscope 2 is formed of a combination of an ultrasound probe and an endoscopic observation unit having an imaging element and an observation optical system formed of a lens or the like, and has an endoscopic observation function and an ultrasound observation function. The ultrasound endoscope 2 has, at a distal end portion thereof, an ultrasound transducer that converts an electric pulse signal received from the ultrasound observation device 3 into ultrasound pulses (acoustic pulses), emits the ultrasound pulses to a subject, converts ultrasound echoes reflected by the subject into an electric signal representing the ultrasound echoes as change in voltage, and outputs the echo signal. A configuration of the ultrasound transducer will be described later.

The ultrasound endoscope 2 has an imaging optical system and an imaging element, is inserted in the gastrointestinal tract (the esophagus, stomach, duodenum, and large intestine) or respiratory organs (the trachea and bronchus) of a subject, and is able to capture images of the gastrointestinal tract or respiratory organs. Furthermore, by using ultrasound, the ultrasound endoscope 2 is able to capture images of organs surrounding the gastrointestinal tract or respiratory organs (such as the pancreas, cholecystis, biliary duct, biliary tract, lymph nodes, mediastinal organs, and blood vessels). Moreover, the ultrasound endoscope 2 has a light guide that guides illumination light to be emitted to the subject at the time of optical imaging. This light guide has a distal end portion that reaches a distal end of an insertion portion to be inserted into the subject of the ultrasound endoscope 2, and a proximal end portion connected to the light source device 6 that generates the illumination light.

The ultrasound endoscope 2 includes, as illustrated in FIG. 1, an insertion portion 21, an operating unit 22, a universal cable 23, and a connector 24. The insertion portion 21 is a part to be inserted into a subject. This insertion portion 21 includes, as illustrated in FIG. 1: a rigid member 211 having an ultrasound transducer 10 provided at a distal end side of the insertion portion 21; a bending portion 212 that is connected to the rigid member 211 at a proximal end side of the rigid member 211 and is bendable; and a flexible tube portion 213 that is connected to the bending portion 212 at a proximal end side of the bending portion 212 and has flexibility. Although specific illustration thereof in the drawings has been omitted, the light guide that transmits illumination light supplied from the light source device 6, and plural signal cables that transmit various signals have been laid inside the insertion portion 21, and a surgical tool insertion passage for insertion of a surgical tool therethrough has been formed inside the insertion portion 21.

Figure 2:
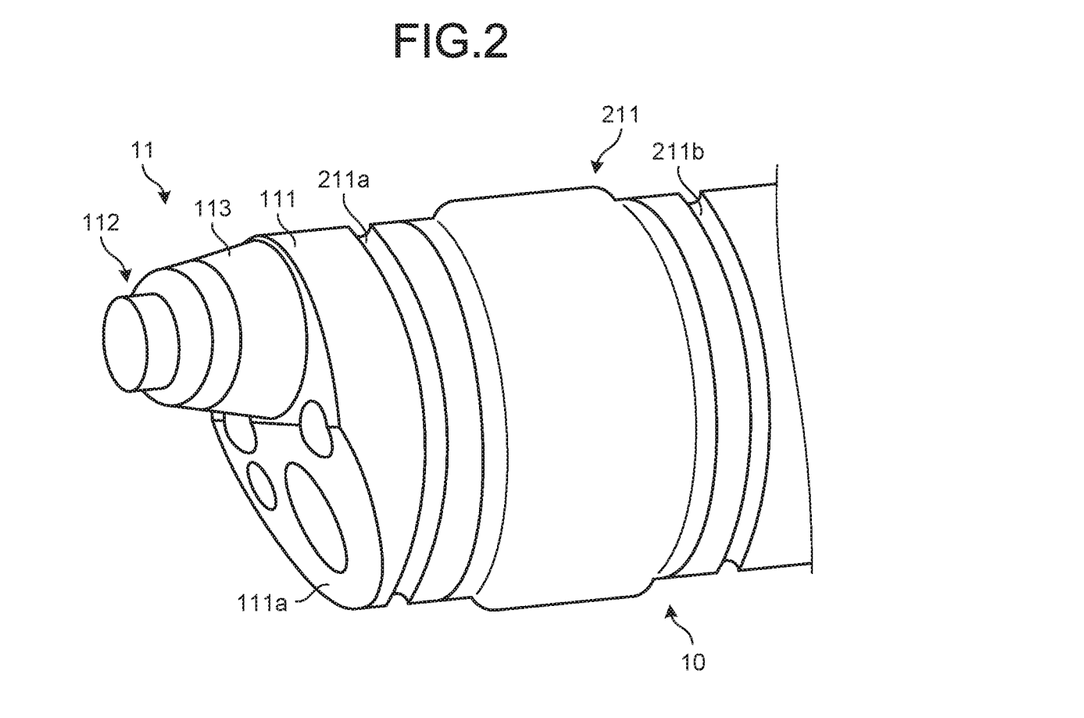
FIG. 2 is a perspective view schematically illustrating a configuration of a distal end of an insertion portion of an ultrasound endoscope according to the first embodiment of the disclosure.
Figure 3:
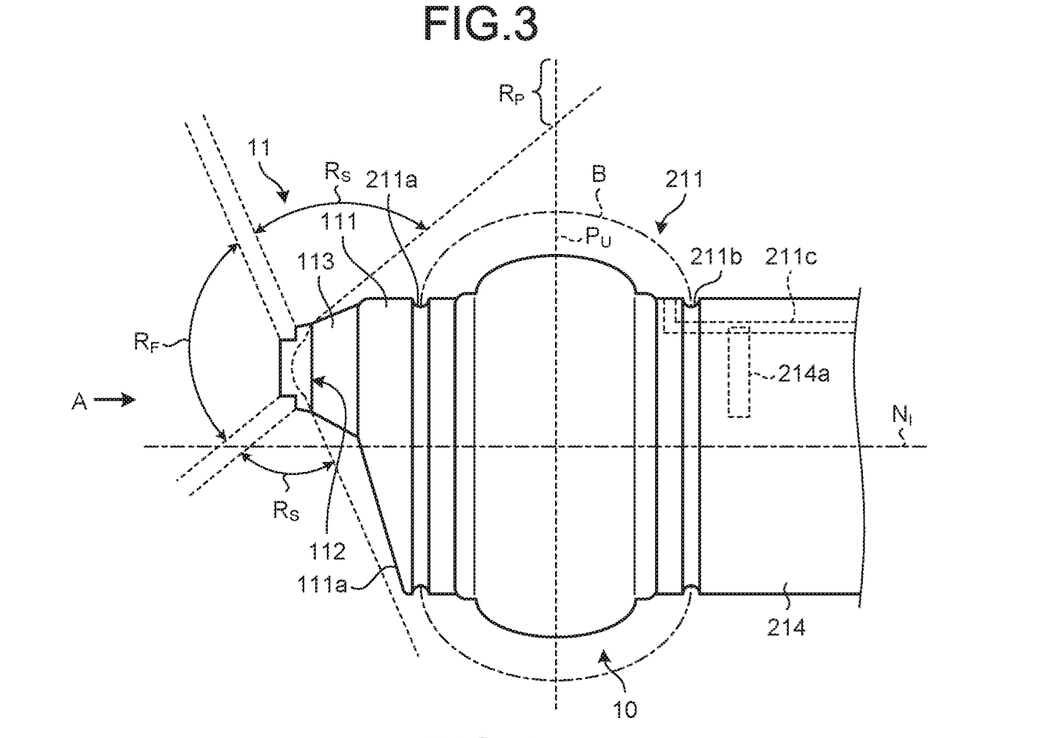
FIG. 3 is a side view schematically illustrating the configuration of the distal end of the insertion portion of the ultrasound endoscope according to the first embodiment of the disclosure.
Figure 4:
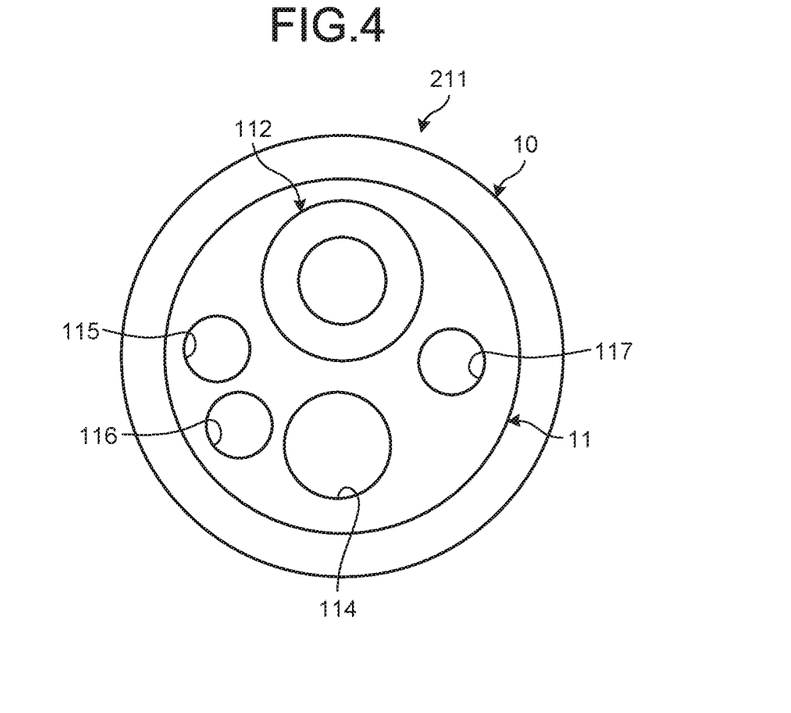
FIG. 4 is a plan view as viewed in a direction of an arrow A in FIG. 3.

FIG. 2 is a perspective view schematically illustrating a configuration of the distal end of the insertion portion of the ultrasound endoscope according to the first embodiment, and is a diagram illustrating a configuration of the rigid member 211. FIG. 3 is a side view schematically illustrating the configuration of the distal end of the insertion portion of the ultrasound endoscope according to the first embodiment of the disclosure, and is a diagram illustrating the configuration of the rigid member 211. FIG. 4 is a plan view as viewed in a direction of an arrow A in FIG. 3.

The rigid member 211 has: the ultrasound transducer 10 described above; and an observation unit 11, which is provided at a distal end side of the ultrasound transducer 10, and which observation light for generating an in-vivo image of a subject enters. Furthermore, the rigid member 211 respectively has balloon retaining portions 211a and 211b respectively formed on the distal end side and a proximal end side of the ultrasound transducer 10, the balloon retaining portions 211a and 211b being able to retain one end and another end of a balloon B that is able to be filled with an ultrasound medium.

The ultrasound transducer 10 is a radial transducer that moves a position to be irradiated with ultrasound for scanning, by emitting the ultrasound in a direction perpendicular to a longitudinal direction (for example, a central axis $N_I$ direction) of the insertion portion 21, around an axis parallel to the longitudinal direction. The ultrasound transducer 10 has plural piezoelectric elements arranged in a circumferential direction thereof, and performs electronic scanning by electronically changing the piezoelectric elements involved in transmission and reception, or delaying transmission and reception of the piezoelectric elements. By the piezoelectric elements vibrating due to input of a pulse signal, the ultrasound transducer 10 irradiates a target to be observed, with ultrasound. Furthermore, the ultrasound reflected from the target to be observed is transmitted to the piezoelectric elements. The piezoelectric elements are vibrated by the transmitted ultrasound, the piezoelectric elements convert the vibration into an electric echo signal, and outputs the echo signal to the ultrasound observation device 3 via a wiring not illustrated.

By sequentially vibrating the piezoelectric elements, the ultrasound transducer 10 sequentially emits ultrasound in the circumferential direction, and receives ultrasound echoes reflected by the target to be observed. That is, the ultrasound transducer 10 receives ultrasound echoes forming a cross sectional image of a scan plane $P_U$ that is around the ultrasound transducer 10 and that is annular. Furthermore, a middle portion of an outer surface of the ultrasound transducer 10 along the longitudinal direction of the insertion portion 21 protrudes in the direction perpendicular to the longitudinal direction, as compared to both of end portions of the outer surface of the ultrasound transducer 10 in the longitudinal direction. The ultrasound transducer 10 has, for example, an acoustic lens forming the outer surface. The acoustic lens is convexed toward the middle portion, has a function of narrowing ultrasound, and emits ultrasound transmitted by the piezoelectric elements to the outside, or takes in ultrasound echoes from the outside. According to the description of the first embodiment, the ultrasound transducer 10 forms a convex shape, but the ultrasound transducer 10 may form a concave shape.

The observation unit 11 has a proximal portion 111 connected to a distal end of the ultrasound transducer 10, and an observation optical system 112 that observation light for generating an in-vivo image of a subject enters.

The proximal portion 111 has a holding portion 113 that holds the observation optical system 112 at a distal end of the holding portion 113. Furthermore, the proximal portion 111 has, formed therein: a surgical tool channel 114, through which a surgical tool is made to protrude from the insertion portion 21, and through which fluid, such as liquid or gas in a subject, is sucked, the surgical tool channel 114 communicating with the surgical tool insertion passage formed in the insertion portion 21; an air and water feeding duct 115, which has a nozzle arranged at a distal end of the air and water feeding duct 115, and through which fluid, such as liquid or gas, is fed into the subject; and illumination openings 116 and 117 where a distal end of the light guide that guides the illumination light, and an illumination lens are arranged.

Figure 5:
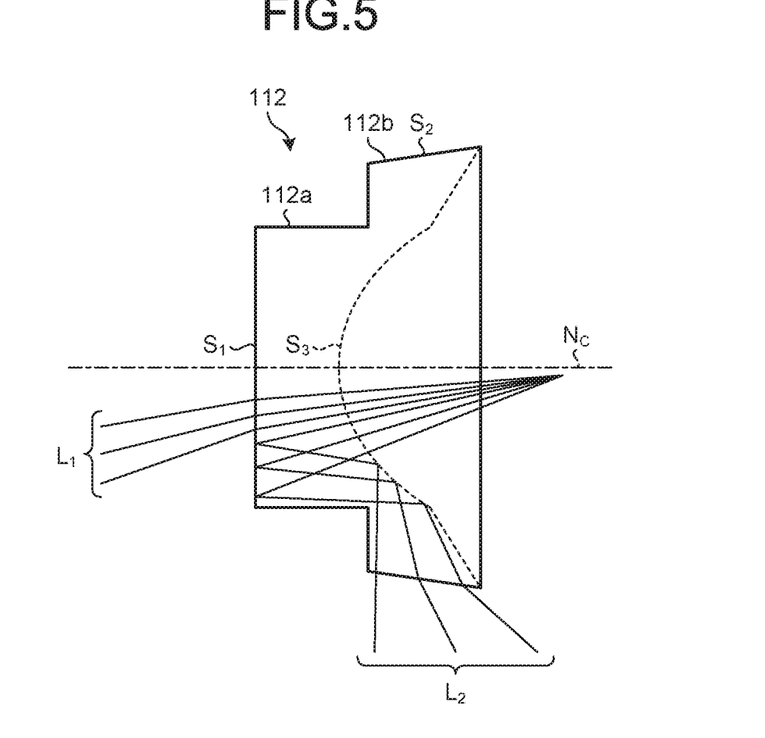
FIG. 5 is a diagram schematically illustrating a configuration of an observation optical system included in the insertion portion of the ultrasound endoscope according to the first embodiment of the disclosure.

FIG. 5 is a diagram schematically illustrating a configuration of the observation optical system included in the insertion portion of the ultrasound endoscope according to the first embodiment of the disclosure. The observation optical system 112 is formed by using a material having optical transparency, and extends in a stepped shape along a central axis $N_C$ direction. Specifically, the observation optical system 112 has: a forward field optical portion 112$a$ that is cylindrical; and a side field optical portion 112$b$ having a minimum diameter larger than a diameter of the forward field optical portion 112$a$, the minimum diameter being in a direction orthogonal to the central axis $N_C$. The forward field optical portion 112$a$ has a forward field incident surface $S_1$, which is a surface intersecting the central axis $N_C$, and which observation light (for example, a light beam group $L_1$) of a forward field range $R_F$ (see FIG. 3) enters. The side field optical portion 112$b$ has a side field incident surface $S_2$, which is a surface intersecting an axis that is in a direction orthogonal to the central axis $N_C$, and which observation light (for example, a light beam group $L_2$) of a side field range $R_s$ (see FIG. 3) enters. Furthermore, a light condensing surface $S_3$ that refracts and condenses observation light entering from each of the forward field incident surface $S_1$ and the side field incident surface $S_2$ is formed inside the observation optical system 112. The observation light entering from the side field incident surface $S_2$ is reflected by a back surface of the forward field incident surface $S_1$ and then enters the light condensing surface $S_3$. The observation light condensed by the light condensing surface $S_3$ is guided via a relay lens or the like, and enters an image sensor 214$a$ arranged at an image formation position of a subject image. The image sensor 214$a$ is provided, for example, as illustrated in FIG. 3, inside an annular member 214 described later.

The side field range $R_S$ includes a part of the scan plane $P_U$ of the ultrasound transducer 10 (for example, a region $R_P$ illustrated in FIG. 3). The side field range $R_S$ preferably includes a focal position of ultrasound transmitted by the ultrasound transducer 10.

Furthermore, the proximal portion 111 has an inclined surface 111$a$ formed therein, the inclined surface 111$a$ being in a region different from a region where the holding portion 113 is formed and being inclined from the distal end side toward a proximal end side of the insertion portion 21. The proximal portion 111 and the side field range $R_S$ do not interfere with each other, due to this inclined surface 111$a$.

The image sensor 214$a$ is realized by using, for example, a charge coupled device (CCD) image sensor, or a complementary metal oxide semiconductor (CMOS) image sensor. The image sensor 214$a$ generates an electric signal by photoelectrically converting received observation light, and inputs the electric signal into the endoscopic observation device 4 via the universal cable 23, the connector 24, and a video cable 41 described later. According to the description of the first embodiment, it is assumed that observation light that has passed through the forward field incident surface $S_1$ and has been formed into an image, and observation light that has passed through the side field incident surface $S_2$ and has been formed into an image enter different regions of the single (the same) image sensor 214$a$.

According to this first embodiment, the balloon retaining portion 211$a$ is provided in the proximal portion 111, and the balloon retaining portion 211$b$ is provided in the annular member 214 that is provided closer to the proximal side of the rigid member 211 than the ultrasound transducer 10 and is rigid. The annular member 214 has a tubular shape enabling a cable extending out from the ultrasound transducer 10 and a cable extending out from the image sensor 214$a$ to be inserted therethrough. Furthermore, the annular member 214 has a balloon duct 211$c$ formed therein, through which air is fed into a balloon that has been attached to the balloon retaining portions 211$a$ and 211$b$. The proximal portion 111 and the annular member 214 are each preferably formed by using an insulating material. According to this first embodiment, the proximal portion 111 corresponds to a first component and the annular member 214 corresponds to a second component. The balloon duct 211$c$ will be described as having an opening that communicates with the outside and is formed on a surface of the annular member 214, but the balloon duct 211$c$ may have any opening formed between the balloon retaining portion 211$a$ and the balloon retaining portion 211$b$. The proximal portion 111 and the annular member 214 may be separately formed, or may be formed integrally with each other via the ultrasound transducer 10.

The operating unit 22 illustrated in FIG. 1 is a portion, which is connected at the proximal end side of the insertion portion 21 and receives various operations from a medical doctor or the like. This operating unit 22 includes, as illustrated in FIG. 1, a bending knob 221 for performing a bending operation on the bending portion 212, and plural operating members 222 for performing various operations. Furthermore, the operating unit 22 has a surgical tool insertion opening 223 formed therein, the surgical tool insertion opening 223 communicating with the surgical tool insertion passage and being for inserting a surgical tool into the surgical tool insertion passage.

The universal cable 23 is a cable that extends from the operating unit 22, and has, arranged therein, plural signal cables that transmit various signals and an optical fiber that transmits illumination light supplied from the light source device 6.

The connector 24 is provided at a distal end of the universal cable 23. The connector 24 includes first to third connector portions 241 to 243, to which an ultrasound cable 31, the video cable 41, and the light source device 6 are respectively connected.

The ultrasound observation device 3 is electrically connected to the ultrasound endoscope 2 via the ultrasound cable 31 (see FIG. 1); and outputs a pulse signal to the ultrasound endoscope 2 and inputs an echo signal from the ultrasound endoscope 2, via the ultrasound cable 31. The ultrasound observation device 3 generates an ultrasound image by performing predetermined processing on the echo signal.

The endoscopic observation device 4 is electrically connected to the ultrasound endoscope 2 via the video cable 41 (see FIG. 1), and receives an image signal from the ultrasound endoscope 2 via the video cable 41. The endoscopic observation device 4 generates an endoscopic image by performing predetermined processing on the image signal.

The display device 5 is formed by use of liquid crystal or organic electroluminescence (EL), and displays thereon the ultrasound image generated by the ultrasound observation device 3 or the endoscopic image generated by the endoscopic observation device 4.

Figure 6:
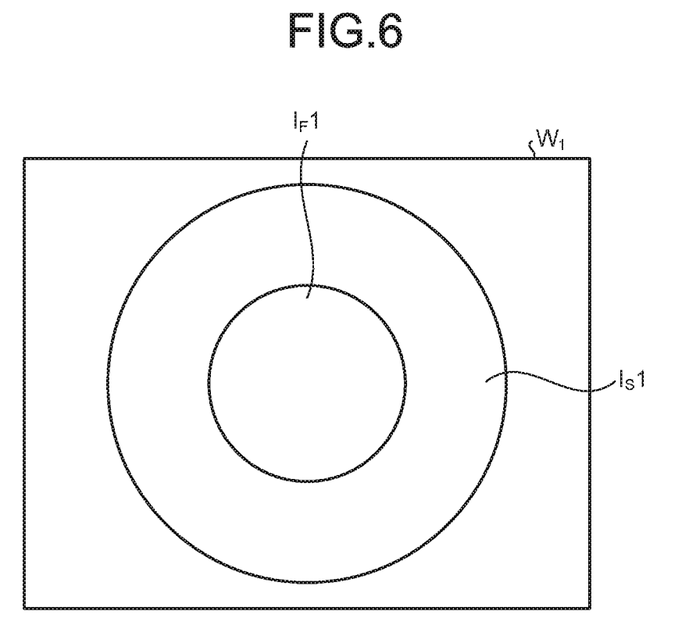
FIG. 6 is a diagram illustrating an example of an image displayed by a display device of the endoscope system according to the first embodiment of the disclosure.

FIG. 6 is a diagram illustrating an example of an image displayed by the display device of the endoscope system according to the first embodiment of the disclosure. FIG. 6 illustrates an image $W_1$ generated by the endoscopic observation device 4 and resulting from observation light acquired by the observation optical system 112. The image $W_1$ includes: a forward field image $I_F1$ resulting from observation light that has passed through the forward field incident surface $S_1$ and has been formed into an image; and a side field image $I_S1$ resulting from observation light that has passed through the side field incident surface $S_2$ and has been formed into an image. In the image $W_1$, each of the forward field image $I_F1$ and the side field image $I_S1$ has been subjected to image processing, such as mask processing, and the side field image $I_S1$ having an annular shape is arranged on the outer periphery of the forward field image $I_F1$ having a circular outer edge. Furthermore, since the side field range $R_S$ includes a part of the scan plane $P_U$ of the ultrasound transducer 10, a scan position of the ultrasound transducer 10 is able to be checked from the side field image $I_S1$.

Figure 7:
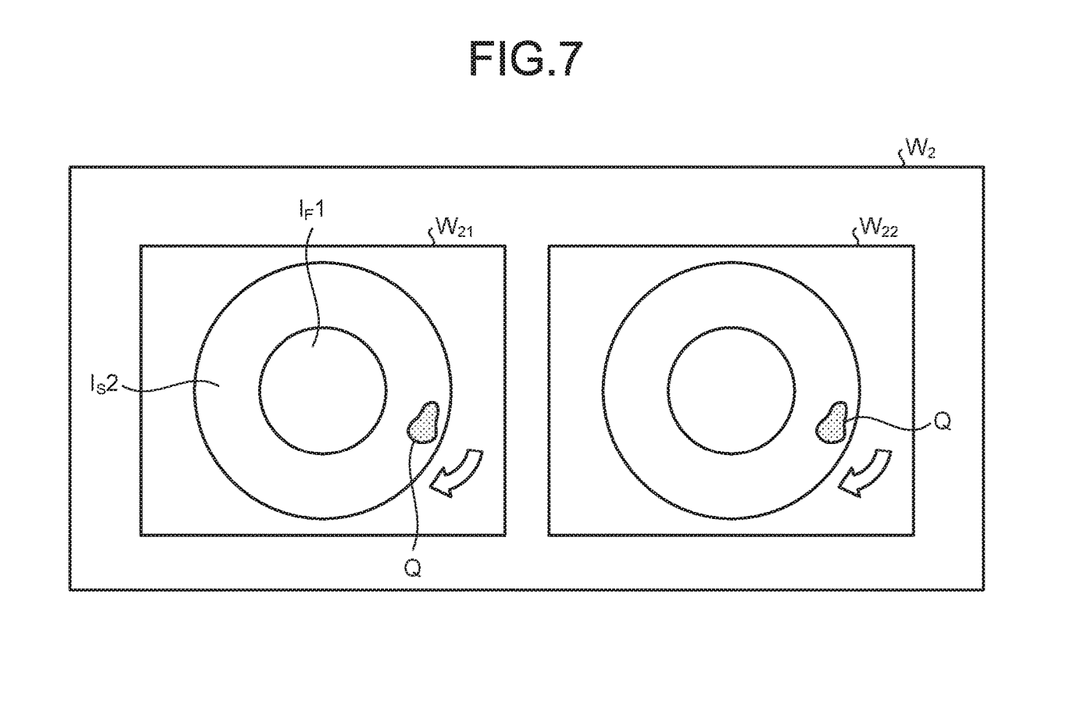
FIG. 7 is a diagram illustrating an example of an image displayed by the display device of the endoscope system according to the first embodiment of the disclosure.
Figure 8:
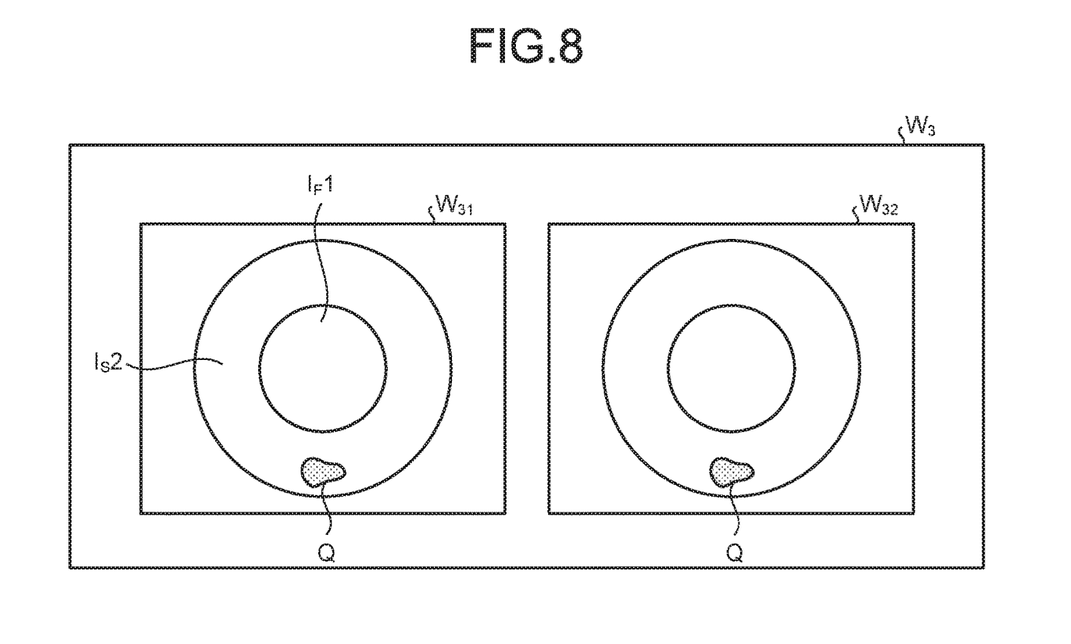
FIG. 8 is a diagram illustrating an example of an image displayed by the display device of the endoscope system according to the first embodiment of the disclosure.

Furthermore, when an ultrasound image acquired by the ultrasound transducer 10 has been rotated such that a region of interest is placed at a desired position, an image acquired by the observation optical system 112 may be rotated in accordance with that movement of the ultrasound image. FIG. 7 and FIG. 8 are each a diagram illustrating an example of an image displayed by the display device of the endoscope system according to the first embodiment of the disclosure. An image $W_2$ illustrated in FIG. 7 includes: an endoscopic image $W_{21}$ having the forward field image $I_F1$ and a side field image $I_S2$, and an ultrasound image $W_{22}$ acquired by the ultrasound transducer 10. When the endoscopic image $W_{21}$ and the ultrasound image $W_{22}$ are being displayed on the display device 5 as illustrated in FIG. 7, if the ultrasound image $W_{22}$ is rotated due to an operation by a user such that a region of interest Q in the ultrasound image $W_{22}$ is positioned lower in the ultrasound image $W_{22}$, the side field image $I_S2$ is rotated in accordance with that rotation. As a result, the region of interest Q (see FIG. 7) captured in both the ultrasound image $W_{22}$ and the side field image $I_S2$ moves lower in these images (see FIG. 8), like in an endoscopic image $W_{31}$ and an ultrasound image $W_{32}$ in an image $W_3$. As this happens, the forward field image $I_F1$ is similarly rotated. Furthermore, in this case, the display and rotation of the ultrasound image $W_{22}$ are controlled by the ultrasound observation device 3, and the display and rotation of the forward field image $I_F1$ and the side field image $I_S2$ are controlled by the endoscopic observation device 4. The ultrasound observation device 3 and the endoscopic observation device 4 perform control of the displayed images in synchronization with each other.

The light source device 6 illustrated in FIG. 1 supplies illumination light to the ultrasound endoscope 2.

According to the above described first embodiment, in the observation optical system 112 where observation light of the forward field range $R_F$ and observation light of the side field range $R_S$ enter, the side field range $R_S$ is made to include a part of the scan plane $P_U$ of the ultrasound transducer 10; and thus a scan position of the ultrasound transducer 10 is able to be checked from a display image (the side field image $I_S1$) of the side field range $R_S$, and the region irradiated with ultrasound by the radial ultrasound transducer is able to be observed through the endoscopic image. As a result, a position targeted in a subject is able to be irradiated with ultrasound infallibly.

Furthermore, according to the above described first embodiment, observation light of the forward field range $R_F$ and observation light of the side field range $R_S$ that are incident on the observation optical system 112 are received by a single image sensor and subjected to signal processing; and thus the insertion portion 21 of the ultrasound endoscope 2, a processing circuit provided therein, and the connector 24 are able to be downsized. Furthermore, since signal processing is performed on signals from a single image sensor, two images (the forward field image $I_F1$ and the side field image $I_S1$) are able to be generated easily.

According to the above description of the first embodiment, observation light that has passed through the forward field incident surface $S_1$ and has been formed into an image, and observation light that has passed through the side field incident surface $S_2$ and has been formed into an image enter different regions of the same image sensor 214a, but they may respectively enter different image sensors. Furthermore, observation light that has been formed into an image may be caused to be incident on an image sensor provided in the operating unit 22 by being guided by an optical fiber or the like.

Furthermore, according to the above description of the first embodiment, the observation optical system 112 is provided with its own optical axis offset from the central axis of the insertion portion 21, but the optical axis may be provided to coincide with the central axis of the insertion portion 21. In this case, the inclined surface 111a is formed over the whole circumference of the proximal portion 111 at an outer edge side thereof, in accordance with the field range of the side field optical portion 112b.

Furthermore, in the above described example according to the first embodiment, the side field image $I_S2$ is rotated correspondingly to the rotation of the ultrasound image, but the side field image $I_S2$ may be rotated such that a position selected in the side field image $I_S2$ is positioned upper in the image $W_3$ and the ultrasound image may be rotated correspondingly to this rotation. That is, in this case, the ultrasound image is rotated in accordance with the position selected in the endoscopic image.

Furthermore, according to the above description of the first embodiment, like the image $W_2$ illustrated in FIG. 7, the endoscopic image $W_{21}$ and the ultrasound image $W_{22}$ are displayed in the same size, but one of these may be displayed larger than the other. If the direction of the viewpoint for the forward field image $I_F1$ is opposite to the direction of the viewpoint for the ultrasound image $W_{22}$, the ultrasound image $W_{22}$ is preferably generated by reversing the image generated from the received echo signal. Furthermore, the endoscopic image $W_{21}$ and the ultrasound image $W_{22}$ acquired at the same time may be concurrently displayed, or displayed at different times.

First Modified Example of First Embodiment

Figure 9:
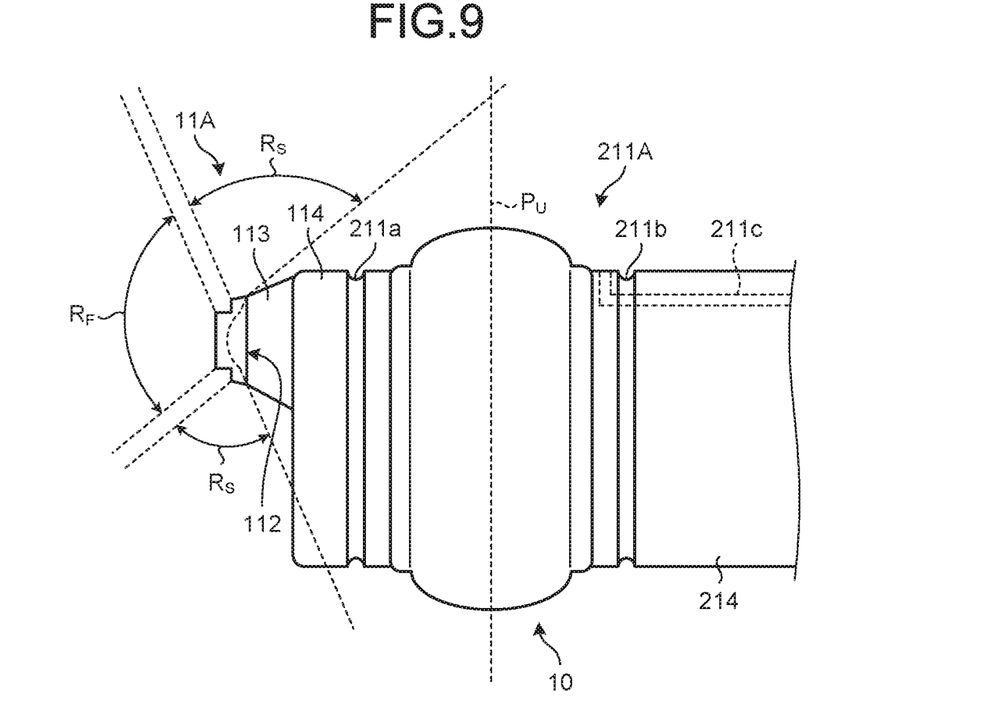
FIG. 9 is a side view schematically illustrating a configuration of a distal end of an insertion portion of an ultrasound endoscope according to a first modified example of the first embodiment of the disclosure.

FIG. 9 is a side view schematically illustrating a configuration of a distal end of an insertion portion of an ultrasound endoscope according to a first modified example of the first embodiment of the disclosure. In the above described example according to the first embodiment, the image of the side field range $R_S$ is formed by making the proximal portion 111 and the side field range $R_S$ not interfere with each other through formation of the inclined surface 111a on the proximal portion 111, but in this first modified example, a proximal portion 114 and the side field range $R_S$ interfere with each other. A rigid member 211A according to the first modified example includes, instead of the observation unit 11, an observation unit 11A.

The observation unit 11A has: the proximal portion 114 that is connected to the ultrasound transducer 10 and is cylindrical; and the above described observation optical system 112 and holding portion 113. The proximal portion 114 is configured without the inclined surface 111a formed in the above described proximal portion 111.

According to the first modified example, the proximal portion 114 does not have the inclined surface 111a formed therein, and thus the proximal portion 114 and the side field range $R_S$ interfere with each other. Therefore, a part of observation light in the side field range $R_S$ is blocked.

Figure 10:
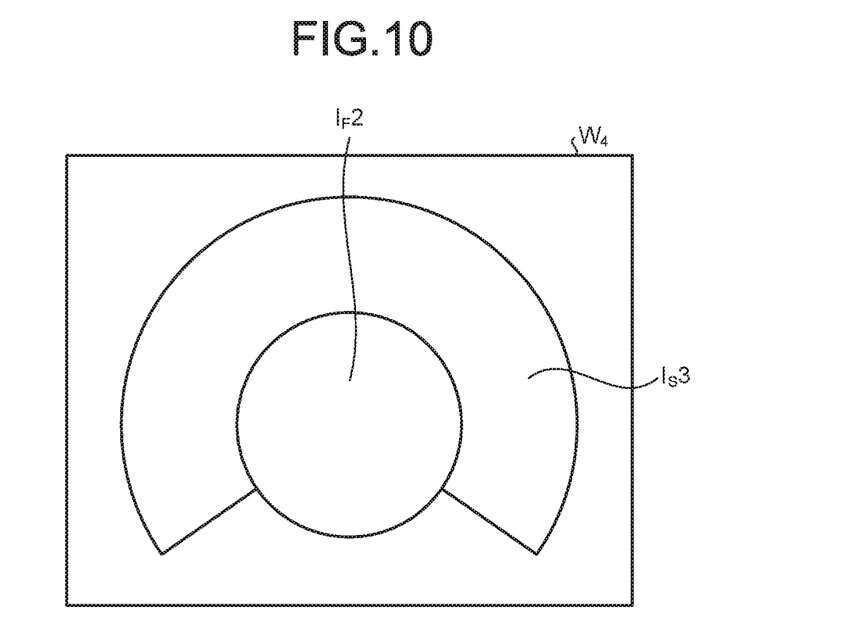
FIG. 10 is a diagram illustrating an example of an image displayed by a display device of an endoscope system according to the first modified example of the first embodiment of the disclosure.

In this first modified example, the endoscopic observation device 4 generates a side field image having a masked part corresponding to an image of a region where the observation light is blocked. FIG. 10 is a diagram illustrating an example of an image displayed by a display device of an endoscope system according to the first modified example of the first embodiment of the disclosure. FIG. 10 illustrates an image $W_4$ generated by the endoscopic observation device 4 and resulting from observation light acquired by the observation optical system 112. The image $W_4$ includes: a forward field image $I_F2$ resulting from observation light that has passed through the forward field incident surface $S_1$ and has been formed into an image; and a side field image $I_S3$ that is a side field image resulting from observation light that has passed through the side field incident surface $S_2$ and has been formed into an image and having a masked region where the observation light is blocked.

As illustrated in FIG. 10, by generating the side field image $I_S3$ such that a part of the side field incident surface $S_2$ is not displayed, the forward field image $I_F2$ and the side field image $I_S3$ are able to be displayed largely, as compared to those in the above described image $W_1$.

According to the description of the first modified example, the side field image $I_S3$ having the masked region where the observation light is blocked is generated, but without masking the region where the observation light is blocked, a side field image having a part of the rigid member 211A captured therein may be generated. Furthermore, on the scan plane $P_U$ of the ultrasound transducer 10, scanning may be performed correspondingly to a side field image that has been generated. That is, the ultrasound transducer 10 may scan a region on the scan plane and corresponding to an endoscopic image, specifically, a region excluding a region corresponding to a masked region of a side field image.

Second Modified Example of First Embodiment

Figure 11:
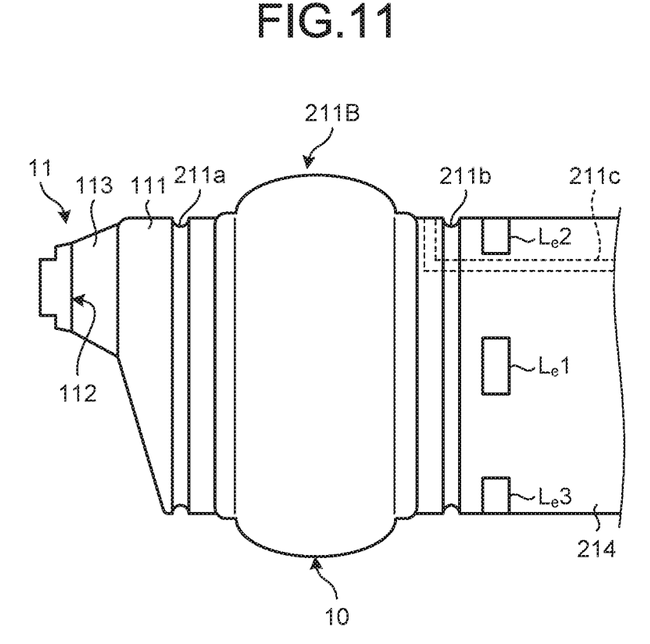
FIG. 11 is a side view schematically illustrating a configuration of a distal end of an insertion portion of an ultrasound endoscope according to a second modified example of the first embodiment of the disclosure.

FIG. 11 is a side view schematically illustrating a configuration of a distal end of an insertion portion of an ultrasound endoscope according to a second modified example of the first embodiment of the disclosure. In this second modified example, light sources that emit illumination light are provided on a side surface of the above described rigid member 211. A rigid member 211B illustrated in FIG. 11 includes, in addition to the above described ultrasound transducer 10 and observation unit 11, four light sources (FIG. 11 illustrating only light sources Le1 to Le3).

The four light sources are arranged at equal intervals along a circumferential direction of the rigid member 211B in the annular member 214. Furthermore, the four light sources are provided closer to the proximal side of the insertion portion 21 in the longitudinal direction than the balloon retaining portion 211b. The four light sources emit illumination light in a direction orthogonal to the longitudinal direction of the insertion portion 21. As a result, a subject in the side field range $R_S$ is illuminated. Each of the light sources is formed by using, for example, a light emitting diode (LED). According to the above description of the second modified example, the number of the light sources used is four, but the number of light sources is not limited to four as long as a subject in the side field range $R_S$ is able to be illuminated.

According to this second modified example, a subject in the side field range $R_S$ is illuminated by four light sources (for example, the light sources Le1 to Le3), and thus as compared to the above described configuration according to the first embodiment, a bright side field image is able to be acquired.

Second Embodiment

Figure 12:
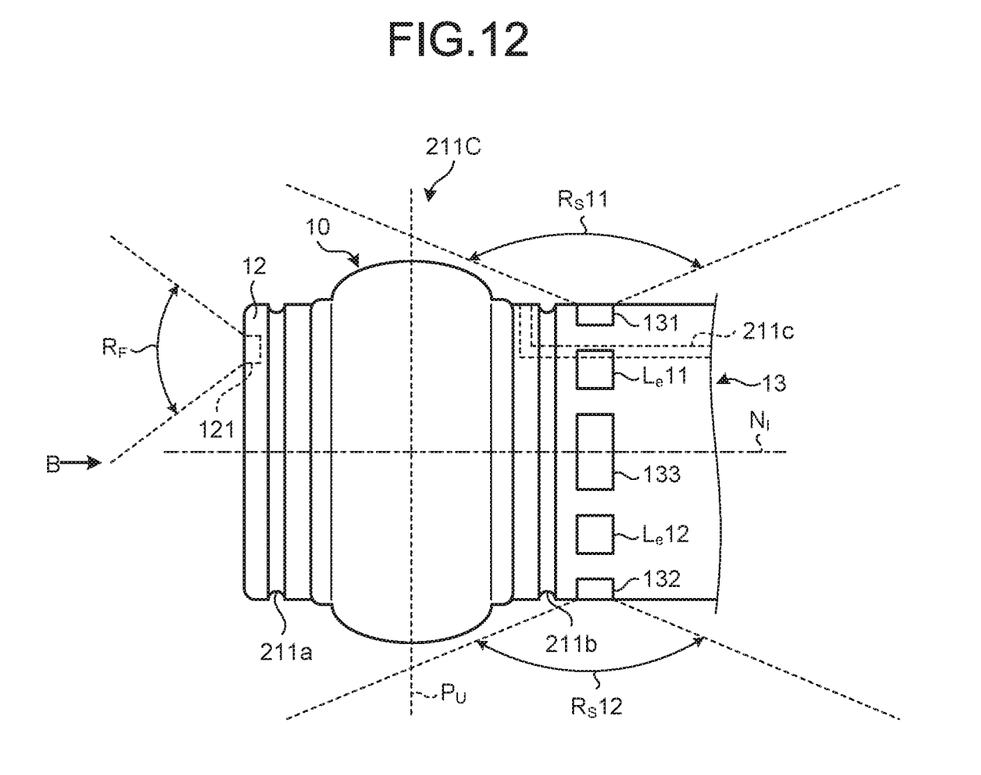
FIG. 12 is a side view schematically illustrating a configuration of a distal end of an insertion portion of an ultrasound endoscope according to a second embodiment of the disclosure.
Figure 13:
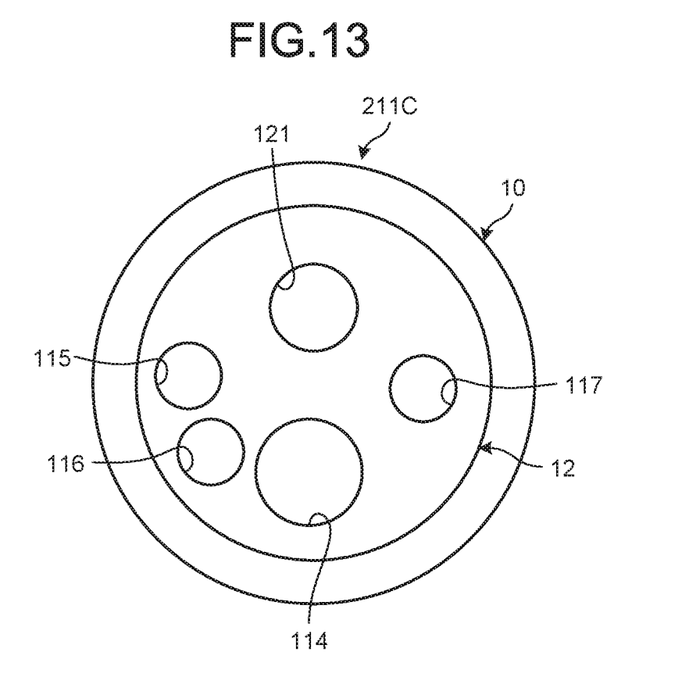
FIG. 13 is a plan view as viewed in a direction of an arrow B in FIG. 12.

FIG. 12 is a side view schematically illustrating a configuration of a distal end of an insertion portion of an ultrasound endoscope according to a second embodiment of the disclosure. FIG. 13 is a plan view as viewed in a direction of an arrow B in FIG. 12. In the above described example according to the first embodiment, the side field optical portion 112b is provided at a distal end of the rigid member 211, but according to this second embodiment, a side field optical portion is provided at a proximal end side of a rigid member.

A rigid member 211C illustrated in FIG. 12 has: the above described ultrasound transducer 10; a first observation unit 12, which is provided at the distal end side of the ultrasound transducer 10, and which observation light for generating an in-vivo forward field image of a subject enters; and a second observation unit 13, which is provided at the proximal end side of the ultrasound transducer 10, and which observation light for generating an in-vivo side field image of the subject enters. Furthermore, the rigid member 211C has the balloon retaining portions 211a and 211b formed therein, which are able to retain a balloon, at positions that are opposite to each other via the ultrasound transducer 10. Moreover, the first observation unit 12 and the ultrasound transducer 10 have been positioned by a known positioning method, such as positioning by use of markers, or positioning by fitting between convexity and concavity.

According to this second embodiment, the balloon retaining portion 211a is provided in the first observation unit 12, and the balloon retaining portion 211b is provided in the second observation unit 13. The second observation unit 13 has a cylindrical shape like the above described annular member 214, such that a cable extending out from the ultrasound transducer 10, and an optical system or a fiber that relays observation light entering from the first observation unit 12 are able to be inserted through the second observation unit 13 and the above described image sensor 214a is able to be held by the second observation unit 13. Furthermore, the second observation unit 13 has, formed therein, the balloon duct 211c, through which air is fed into the balloon attached to the balloon retaining portions 211a and 211b. The first observation unit 12 and the second observation unit 13 are each preferably formed by using an insulating material. Moreover, the first observation unit 12 and the second observation unit 13 have been positioned by a known positioning method, such as positioning by use of markers. According to this second embodiment, the first observation unit 12 corresponds to the first component or a component, and the second observation unit 13 corresponds to the second component.

The first observation unit 12 has a forward field optical portion 121, which is formed by using one or plural lenses, and which observation light for generating an in-vivo forward field image of a subject enters. Furthermore, as illustrated in FIG. 13, the first observation unit 12 has: the surgical tool channel 114, which communicates with the surgical tool insertion passage formed in the insertion portion 21 and allows a surgical tool to protrude from the distal end of the insertion portion 21, and into which fluid, such as liquid or gas in a subject is sucked; the air and water feeding duct 115, which has a nozzle arranged at a distal end thereof, and through which fluid, such as liquid or gas, is fed into the subject; and the illumination openings 116 and 117 where the distal end of the light guide that guides illumination light and the illumination lens are arranged. The forward field optical portion 121 has an optical axis parallel to the longitudinal direction (for example, the axis $N_I$ direction in FIG. 12) of the insertion portion 21, and observation light of the forward field range $R_F$ enters the forward field optical portion 121.

The first observation unit 12 is formed by using, for example, a metallic material, and a part of the first observation unit 12 has been inserted in the ultrasound transducer 10. The first observation unit 12 and the ultrasound transducer 10 are insulated from each other. The first observation unit 12 may be formed by using insulating resin or the like, or may be covered by an insulating cover. Furthermore, a circumferential position of the forward field optical portion 121 has been positioned with respect to the first observation unit 12, the circumferential position being around an axis parallel to the longitudinal direction of the insertion portion 21. Specifically, a circumferential position of a lens included in the forward field optical portion 121 has been positioned with respect to a casing forming a part of the first observation unit 12, the circumferential position being around the optical axis.

The first observation unit 12 is formed of a first member where the balloon retaining portion 211a is formed and a second member that holds the forward field optical portion 121, and when the first member and the second member have been connected together, the first member and the second member have been positioned with respect to the ultrasound transducer 10. By positioning the first member and the second member, a positional relation in a circumferential direction between the ultrasound transducer 10 and the optical observation unit is determined. The first member and second member may be positioned by a known positioning method, such as positioning by use of markers, or positioning by fitting between convexity and concavity. In this case, the first member corresponds to the first component and the second member corresponds to a third component.

Figure 14:
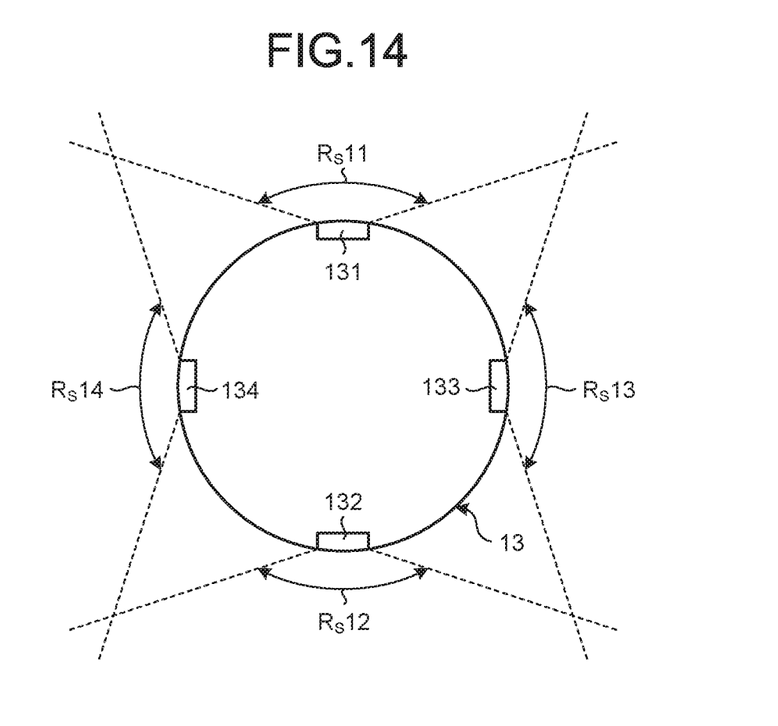
FIG. 14 is a diagram schematically illustrating a configuration of an optical system included in the insertion portion of the ultrasound endoscope according to the second embodiment of the disclosure.

FIG. 14 is a diagram schematically illustrating a configuration of an optical system included in the insertion portion of the ultrasound endoscope according to the second embodiment of the disclosure. The second observation unit 13 has: four side field optical portions 131 to 134, each of which is formed by using one or plural lenses, and which observation light having optical axes that are in a direction orthogonal to the axis $N_I$ and are different from one another enters; and four light sources (FIG. 12 illustrating light sources $L_e11$ and $L_e12$ only) that are provided between adjacent ones of the side field optical portions along a circumferential direction of the rigid member 211C and emit illumination light in a direction orthogonal to the axis $N_I$. For example, observation light of a side field range $R_S11$ and having an optical axis in a direction orthogonal to the axis $N_I$ enters the side field optical portion 131. Furthermore, observation light of a side field range $R_S12$ different from the side field range $R_S11$ and having an optical axis in a direction orthogonal to the axis $N_I$ enters the side field optical portion 132. Observation light of a side field range $R_S13$ different from the side field ranges $R_S11$ and $R_S12$ and having an optical axis in a direction orthogonal to the axis $N_I$ enters the side field optical portion 133. Observation light of a side field range $R_S14$ different from the side field ranges $R_S11$ to $R_S13$ and having an optical axis in a direction orthogonal to the axis $N_I$ enters the side field optical portion 134. The side field ranges $R_S11$ to $R_S14$ are illuminated by illumination light respectively emitted from the four light sources.

The observation light incident on the first observation unit 12 and the second observation unit 13 is condensed by an optical system not illustrated in the drawings, and enters an image sensor (not illustrated in the drawings) arranged at an image formation position. Observation light incident on the respective observation units may enter the same image sensor or may enter different image sensors. Furthermore, an image sensor may be arranged correspondingly to each side field optical portion.

Furthermore, the side field ranges $R_S11$ to $R_S14$ each include a part of the scan plane $P_U$ of the ultrasound transducer 10. The side field ranges $R_S11$ to $R_S14$ preferably include a focal position of ultrasound transmitted by the ultrasound transducer 10.

Figure 15:
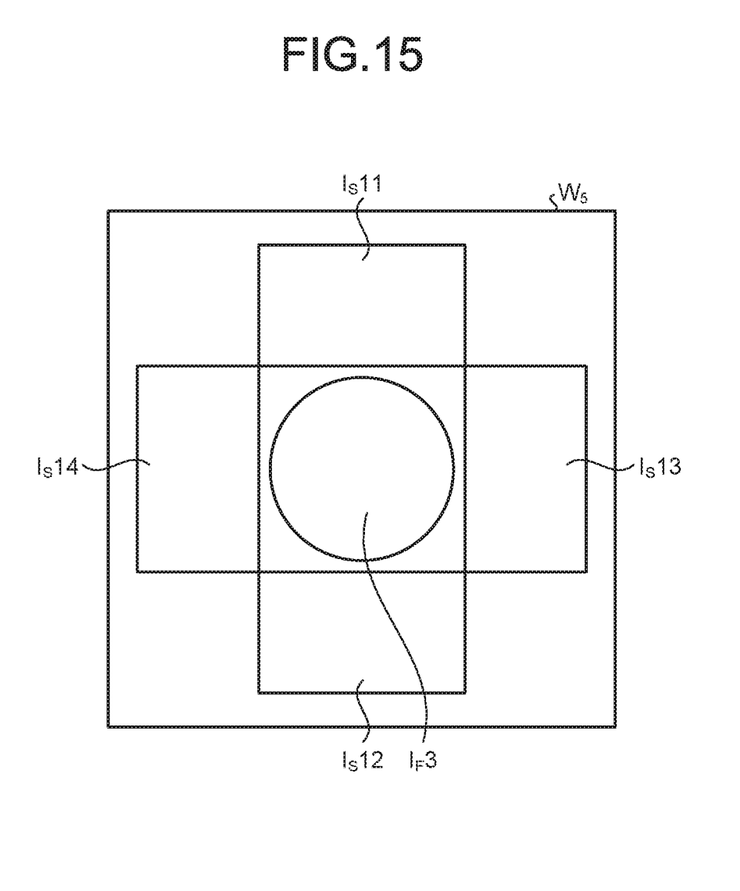
FIG. 15 is a diagram illustrating an example of an image displayed by a display device of an endoscope system according to the second embodiment of the disclosure.

FIG. 15 is a diagram illustrating an example of an image displayed by a display device of an endoscope system according to the second embodiment of the disclosure. FIG. 15 illustrates an image $W_5$ resulting from observation light generated by the endoscopic observation device 4 and acquired by the first observation unit 12 and the second observation unit 13. The image $W_5$ includes a forward field image $I_F3$ resulting from observation light that has passed through the forward field optical portion 121 and has been formed into an image, and side field images $I_S11$ to $I_S14$ resulting from observation light that has passed through the side field optical portions 131 to 134 and has been formed into images. In the image $W_5$, the forward field image $I_F3$ and the side field images $I_S11$ to $I_S14$ have been subjected to image processing, such as mask processing, and the side field images $I_S11$ to $I_S14$ each having a rectangular shape are arranged on the outer periphery of the forward field image $I_F3$ having a circular outer edge. Furthermore, since the side field ranges $R_S11$ to $R_S14$ each include a part of the scan plane $P_U$ of the ultrasound transducer 10, a scan position of the ultrasound transducer 10 is able to be checked from the side field images $I_S11$ to $I_S14$.

Furthermore, when an ultrasound image acquired by the ultrasound transducer 10 is rotated such that a region of interest is placed at a desired position, images acquired by the first observation unit 12 and the second observation unit 13 may be rotated in accordance with that movement of the ultrasound image. When an ultrasound image acquired by the ultrasound transducer 10 is being displayed, together with the image $W_5$ on the display device 5, if the ultrasound image is rotated such that a region of interest in the ultrasound image is positioned lower in the ultrasound image due to an operation by a user, the side field image $I_S11$ to $I_S14$ are rotated in accordance with this rotation. As a result, one of the side field images $I_S11$ to $I_S14$ is moved lower in the image $W_5$, the one having the region of interest captured therein. Upon this movement, the forward field image $I_F3$ is also rotated similarly. Moreover, in this case, the display and rotation of the ultrasound image are controlled by the ultrasound observation device 3, and the display and rotation of the forward field image $I_F3$ and the side field images $I_S11$ to $I_S14$ are controlled by the endoscopic observation device 4. The ultrasound observation device 3 and the endoscopic observation device 4 perform control of the displayed images in synchronization with each other.

According to the above described second embodiment, in the first observation unit 12 where observation light of the forward field range $R_F$ enters, and the second observation unit 13 where observation light of the side field ranges $R_S11$ to $R_S14$ enters, the side field ranges $R_S11$ to $R_S14$ are each made to include a part of the scan plane $P_U$ of the ultrasound transducer 10; and thus a scan position of the ultrasound transducer 10 in a display image of the side field range $R_S$ (the side field images $I_S11$ to $I_S14$) is able to be checked, and a region irradiated with ultrasound by a radial ultrasound transducer is able to be observed through an endoscopic image.

Furthermore, according to the above described second embodiment, the forward field optical portion 121 and the side field optical portions 131 to 134 are able to be formed by using general plate-shaped lenses, and thus optical design and lens machining are able to be simplified as compared to the observation optical system 112 according to the first embodiment.

In the above described example according to the second embodiment, the side field images $I_S11$ to $I_S14$ are rotated in accordance with rotation of an ultrasound image, but one selected from the side field images $I_S11$ to $I_S14$ may be moved upper in the image $W_5$, and an ultrasound image may be rotated in accordance with this movement. In this case, the side field images $I_S11$ to $I_S14$ are made selection candidates (selected positions), and a side field image selected is moved above the forward field image $I_F3$.

Furthermore, according to the above description of the second embodiment, the side field images $I_S11$ to $I_S14$ are displayed separately, but a single annular image (for example, the side field image $I_S1$) may be generated by connecting portions of the side field images $I_S11$ to $I_S14$, the portions being where their field ranges overlap each other.

Thus far, modes for carrying out the disclosure have been described, but the disclosure is not limited only to the above described embodiments and modified examples. Not being limited to the above described embodiments and modified examples, the disclosure may include various embodiments without departing from the technical ideas stated in the claims. Furthermore, any of the components according to the embodiments and modified examples may be combined together as appropriate.

Some embodiments have an effect of enabling, through an endoscopic image, observation of a region irradiated with ultrasound by a radial ultrasound transducer.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope, comprising:
   an insertion portion configured to be inserted into a subject, acquire an optical subject image, and transmit and receive ultrasound;
   an ultrasound transducer configured to emit the ultrasound in a direction perpendicular to a longitudinal direction of the insertion portion, and perform scanning in a circumferential direction of an axis parallel to the longitudinal direction;
   a forward field optical portion provided at a distal end of the insertion portion in the longitudinal direction, the distal end being where observation light coming from a forward field enters; and
   a side field optical portion provided at a distal end side of the insertion portion in the longitudinal direction and is where observation light from a side field including a part of a scan plane of the ultrasound transducer enters, the side field being a field in direction perpendicular to the longitudinal direction; and
   a proximal portion connected to a distal end of the ultrasound transducer, the proximal portion being configured to hold the side field optical portion, wherein
      a distal end of the proximal portion in the longitudinal direction has a surface inclined relative to the longitudinal direction such that the proximal portion does not interfere with the observation light from the side field,
   wherein the side field optical portion has a field that extends over a whole circumference around the axis parallel to the longitudinal direction.

2. The ultrasound endoscope according to claim 1, wherein the field of the side field optical portion includes a focal position of the ultrasound emitted from the ultrasound transducer.

3. The ultrasound endoscope according to claim 1, wherein the forward field optical portion and the side field optical portion are formed of a single optical system.

4. The ultrasound endoscope according to claim 1, wherein the side field optical portion is positioned closer to a proximal end side in the longitudinal direction than the forward field optical portion.

5. The ultrasound endoscope according to claim 1, wherein the ultrasound transducer has, on an outer surface of the ultrasound transducer, a middle portion in the longitudinal direction, the middle portion protruding or being recessed in direction perpendicular to the longitudinal direction with respect to both of end portions of the outer surface in the longitudinal direction.

6. The ultrasound endoscope according to claim 1, further comprising:
   a component that is provided at the distal end of the ultrasound transducer in the longitudinal direction, has a part of the component inserted in the ultrasound transducer, and holds the forward field optical portion, wherein the component is formed of an insulating material.

7. The ultrasound endoscope according to claim 1, further comprising:
a component that is provided at the distal end of the ultrasound transducer in the longitudinal direction, and holds the forward field optical portion, wherein
circumferential positions of the forward field optical portion and the component have been positioned, the circumferential positions being around the axis parallel to the longitudinal direction.

8. The ultrasound endoscope according to claim 1, further comprising:
a first component that is provided at the distal end of the ultrasound transducer in the longitudinal direction, and has a first retaining portion where one end of a balloon that is able to be filled with an ultrasound medium is attached, the first retaining portion having a groove shape; and
a second component that is provided at a proximal end of the ultrasound transducer in the longitudinal direction, and has a second retaining portion where another end of the balloon is attached, the second retaining portion having a groove shape.

9. The ultrasound endoscope according to claim 8, further comprising:
a third component that is provided closer to the distal end of the insertion portion in the longitudinal direction than the first component, the third component configured to hold the forward field optical portion, wherein
the first component and the third component have been positioned with respect to the ultrasound transducer.

10. The ultrasound endoscope according to claim 8, further comprising a light source that is provided closer to a proximal end side in the longitudinal direction than the second retaining portion, the light source being configured to emit illumination light.

11. An ultrasound endoscope system, comprising:
the ultrasound endoscope according to claim 1;
an endoscopic observation device configured to generate an endoscopic image based on observation light incident on the forward field optical portion and the side field optical portion; and
an ultrasound observation device configured to generate an ultrasound image based on ultrasound received by the ultrasound transducer.

12. The ultrasound endoscope according to claim 11, further comprising a display configured to display the endoscopic image and the ultrasound image.

13. The ultrasound endoscope system according to claim 11, wherein the endoscopic observation device is configured to rotate the endoscopic image in accordance with rotation of the ultrasound image by the ultrasound observation device.

14. The ultrasound endoscope system according to claim 11, wherein the ultrasound observation device is configured to rotate the ultrasound image in accordance with a selected position in the endoscopic image.

15. The ultrasound endoscope system according to claim 11, wherein the endoscopic observation device is configured to generate the endoscopic image such that a part of an image acquired by the forward field optical portion is not displayed.

16. The ultrasound endoscope system according to claim 15, wherein the ultrasound transducer is configured to scan the scan plane according to the endoscopic image.

* * * * *